United States Patent [19]

Conway et al.

[11] Patent Number: 4,902,696
[45] Date of Patent: Feb. 20, 1990

[54] SYNERGISTIC INTRAOCULAR PRESSURE LOWERING COMBINATIONS

[75] Inventors: Paul G. Conway, Flemington; Grover C. Helsley, Pluckemin, both of N.J.

[73] Assignee: Hoechst-Roussel Pharmaceuticals, Inc., Somerville, N.J.

[21] Appl. No.: 105,850

[22] Filed: Oct. 8, 1987

[51] Int. Cl.$^4$ .................... A61K 31/35; A61K 31/535; C07D 319/04; C07D 413/06

[52] U.S. Cl. ........................... 514/320; 514/255; 514/321; 514/455; 514/422; 514/232.8; 514/228.2; 514/913; 514/89; 514/91; 514/85; 514/100

[58] Field of Search ............... 514/459, 646, 649, 731, 514/912, 913, 255, 321, 455, 422, 232.8, 228.2, 913, 89, 91, 85, 100

[56] References Cited

U.S. PATENT DOCUMENTS

| 4,088,659 | 5/1978 | Bhat et al. | |
| 4,118,508 | 10/1978 | Bhat et al. | |
| 4,134,986 | 1/1979 | Bajwa et al. | |
| 4,476,140 | 10/1984 | Sears et al. | |
| 4,490,379 | 12/1984 | Podos et al. | 514/913 |
| 4,639,443 | 1/1987 | Kosley et al. | |
| 4,639,446 | 1/1987 | Kosley et al. | |
| 4,666,904 | 5/1987 | Kosley et al. | 514/453 |
| 4,677,103 | 6/1987 | Kosley et al. | 514/452 |
| 4,771,049 | 9/1988 | Kosley et al. | 514/445 |

FOREIGN PATENT DOCUMENTS 0217372 4/1987 European Pat. Off. .
2654796 6/1978 Fed. Rep. of Germany .

Primary Examiner—H. M. S. Sneed
Assistant Examiner—J. Saba
Attorney, Agent, or Firm—Tatsuya Ikeda

[57] ABSTRACT

Herein is described an ocular composition comprising an ocular decongestant such as phenylephrine and certain labdane derivatives which are intraocular pressure lowering agents. The composition not only markedly reduces the ocular reddening otherwise produced by such labdane compounds, but also unexpectedly prolongs and frequently potentiates their intraocular pressure lowering effect. Both of these effects are very beneficial to the use of such labdanes for the treatment of glaucoma.

28 Claims, No Drawings

SYNERGISTIC INTRAOCULAR PRESSURE LOWERING COMBINATIONS

The present invention is directed to an ocular composition comprising an ocular decongestant such as phenylephrine and certain derivatives of labdane depicted by formula I which are intraocular pressure lowering agents. Such combinations not only markedly reduce the ocular reddening (hyperemia) otherwise produced by such labdanes but also unexpectedly prolong and frequently potentiate their intraocular pressure lowering effect. This invention is also directed to a method of lowering intraocular pressure in mammals which comprises administration of a composition comprising an ocular decongestant and a labdane compound of formula I.

The labdane derivatives used in this invention have formula I below,

[Structure of Formula (I)]

wherein
(a) $R_1$ is —H, $$-\overset{O}{\underset{\|}{C}}-R_2, \quad -\overset{O}{\underset{\|}{C}}-NR_3R_4, \quad -\overset{O}{\underset{\|}{C}}-\overset{H}{\underset{R_5}{C}}-NR_3R_4 \quad \text{or} \quad -\overset{R_{10}}{\underset{R_{12}}{Si}}-R_{11},$$

where
$R_2$ is hydrogen, loweralkyl,

[various substituent structures shown]

$-\overset{CH_3}{\underset{CH_2CH_3}{C}}-OH$, [cyclic structures], [furan, tetrahydrofuran, pyrrolidine structures]

[additional structures including pyrrolidinone and nitrophenyl-sulfanyl pyrrolidine, a dioxane-type sugar structure, and $-(CH_2)_m-\overset{O}{\underset{\|}{P}}\overset{R_{13}}{\underset{R_{13}}{\diagdown}}$ or ]

$$-(CH_2)_p-\overset{R_{14}}{\underset{OR_{16}}{\overset{|}{C}}}-R_{15},$$

where
m is 1, 2 or 3, $R_{13}$ is loweralkyl, p is 0, 1, 2 or 3, $R_{14}$, $R_{15}$ and $R_{16}$ are each independently hydrogen or loweralkyl;
$R_3$ is hydrogen, loweralkyl, $-(CH_2)_qOR_{17}$ or $-CH_2CHOHCH_2OH$, where q is 0, 2 or 3 and $R_{17}$ is hydrogen or loweralkyl; $R_4$ is hydrogen, loweralkyl or $-(CH_2)_rOH$ where r is 2 or 3, or alternatively $-NR_3R_4$ as a whole is $$-N\overset{(CH_2)_n}{\underset{\diagdown}{\diagup}}X,$$

where n is 0, 1 or 2 and —X— is $$-\overset{O}{\underset{\|}{C}}-,$$

—O—, —S—, —SO—, —SO$_2$—, $$-\overset{H}{\underset{R_{18}}{\overset{|}{C}}}- \quad \text{or} \quad -\underset{R_{19}}{\overset{|}{N}}-,$$

$R_{18}$ being hydrogen, loweralkyl, loweralkoxy or loweralkylcarbonyloxy, and $R_{19}$ being loweralkyl; $R_5$ is hydrogen, loweralkyl, benzyl or hydroxymethyl; and
$R_{10}$, $R_{11}$ and $R_{12}$ are each independently loweralkyl;
(b) $R_9$ is hydrogen, or alternatively to the above, $R_1$ and $R_9$ taken together form $$-\overset{O}{\underset{\|}{C}}-, \quad -\overset{O}{\underset{\|}{S}}- \quad \text{or} \quad -\overset{H}{\underset{NR_{20}R_{21}}{\overset{|}{C}}}-,$$

where $R_{20}$ and $R_{21}$ are each independently loweralkyl, or alternatively $-NR_{20}R_{21}$ as a whole is

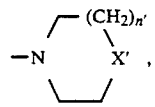

where n' has the same definition as n but is independent thereof and X' has the same definition as X but is independent thereof; and (c) $R_6$ and $R_7$ are each independently —H,

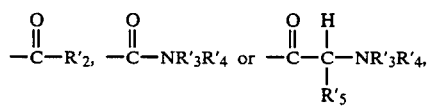

or taken together form

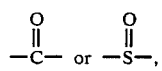

where $R_2'$, $R_3'$, $R_4'$ and $R_5'$ have the same definitions as $R_2$, $R_3$, $R_4$ and $R_5$, respectively, but are independent thereof, respectively.

The compounds of formula I and methods of synthesizing them are disclosed for instance in Bajwa et al., U.S. Pat. No. 4,134,986; U.S. patent application Ser. No. 804,405, filed July 24, 1986 (now U.S. Pat. No. 4,639,446) which is a continuation-in-part of Ser. No. 681,779 filed Dec. 4, 1984; U.S. patent application Ser. No. 848,053 filed Apr. 4, 1986 (now U.S. Pat. No. 4,639,443) which is a continuation-in-part of Ser. No. 707,283 filed Mar. 1, 1985; and U.S. patent application Ser. No. 947,070 filed Apr. 4, 1986.

It is known that the labdane compounds of formula I have the effect of reducing intraocular pressure in mammals. However, when administered topically, they also cause redness (hyperemia) in the eyes, which is very undesirable from the standpoint of practical utility of these compounds.

It has now been found that when an ocular decongestant such as phenylephrine, is used in combination with a labdane compound of formula I, the composition not only markedly reduces the ocular reddening which is otherwise produced by such labdane compounds, but also unexpectedly prolongs and frequently potentiates their intraocular pressure lowering effect. Both of these effects are very beneficial to the use of such labdanes for the treatment of glaucoma.

In this invention, an ocular decongestant (an agent which reduces or suppresses redness in the eye, for instance, phenylephrine) and the labdane compound of formula I are combined in a single dosage form using a suitable vehicle. Typically the concentration of phenylephrine in the ocular composition of this invention is between 0.01% and 3.0% by weight, preferably between 0.12% and 0.20%. Typically the concentration of the labdane compound in the ocular composition is between 0.1% and 1.0% by weight. Any suitable vehicle for ocular compositions known in the art can be used in this invention. An example of such vehicle is shown below.

| An Example of Vehicle | |
|---|---|
| Component | Concentration |
| Benzalkonium chloride | 0.01% |
| Edetate disodium | 0.01% |
| Sodium phosphate monobasic (pH 7.4) | 0.175% |
| Sodium phosphate dibasic (pH 7.4) | 0.81% |
| Sodium chloride | 0.41% |
| HPMC (methocel E-15) | 2.0% |
| Polysorbate 20 | 5.0% |
| Triple distilled water | q.s. 100% |

The ocular composition of this invention is applied topically to the eye using a conventional means such as an eye dropper. A typical amount of administration is three times 20 microliters at two to three minute intervals.

In ascertaining the effect of this invention, samples of ocular composition comprising suitable amounts of phenylephrine and a labdane compound of formula I were prepared and a test was conducted in the following manner.

METHOD

Each New Zealand white rabbit (NZW, 2.0 to 2.5 kg) was acclimated to the laboratory environment and the procedure at least one day prior to experimentation. Acclimation consisted of handling the animal as well as taking IOP (intraocular pressure) measurements in the absence of drug.

IOP measurements consisted of topically administering one drop (approximately 50 microliters) of a short-acting local anesthetic (Ophthaine 0.5%) directly on the eyes of an unrestrained rabbit. Approximately 40–45 seconds following local anesthetic administration, an IOP reading for each eye was taken for 10 seconds and recorded in mmHg. IOP was determined by applanation pneumotonometry using an Alcon pneumatonograph uncalibrated for the rabbit eye.

On the day of the experiment, two baseline IOP measurements were determined and designated as $P_1$ and $P_2$, respectively. The $P_1$ measurement was recorded 30 minutes prior to drug administration while the $P_2$ measurement occurred just prior to drug or placebo administration. The $P_2$ measurement was the designated IOP at zero (0) time and was used as the baseline control value for the determination of percent reduction in outflow pressure. Thus, a baseline value was determined for each rabbit studied.

Immediately following the $P_2$ measurement, the appropriate concentration of drug or vehicle was administered topically to the right eye of the rabbits. This was done by placing three successive 20 microliter additions directly onto the eye at two- to three-minute intervals. In addition, during drug application, the lower eyelid was held so that excess fluid was collected in the exposed conjunctival sac. Simultaneously, the left eye received vehicle with the same regimen as the drug-treated right eye. The vehicle (control) treatment was to monitor potential contralateral ocular effects. Following drug or vehicle treatment, IOP measurements were taken as described above characteristically at the following time periods: 0.5, 1.0, 1.5, 2.0, 3.0, 4.0, 5.0 and 6.0 hours. Additional monitoring was performed as dictated by the response of the drug.

The IOP of each rabbit eye for each time period was initially recorded in mmHg. However, to account for initial IOP differences among rabbits, the changes in mmHg were normalized by converting to percent reduction in outflow pressure (ROP). The ROP was calculated according to an equation proposed by Mishima ("Clinical Pharmacokinetics of the Eye", Invest. Ophthalmol. Vis. Sci. 21, 504–541 (1981)):

$$\% \ ROP = \frac{P_0 - P_e}{P_0 - Ep} \times 100$$

where Po is the IOP reading in mmHg at zero time, Pe is the experimental IOP reading in mmHg at the appropriate time following drug or vehicle administration and Ep is episcleral venous pressure taken as a constant of 10 mmHg. The percent ROP for each rabbit at each time period studied was recorded and grouped to determine a mean percent ROP for each time period as well as the duration of activity.

Phenylephrine hydrochloride (0.12% or 1%) and test drug were combined directly in the aforementioned vehicle.

The experimental IOP measurements were compared statistically to the pretreatment IOP measurements by means of the paired Students t-test, P<0.05.

RESULTS

One effect produced by direct adenylate cyclase stimulators such as labdane compounds of formula I after topical ocular administration is vasodilatation resulting in local hyperemia. To circumvent this effect, such compounds are combined with a low concentration of phenylephrine. Table 1 lists the effects of the drug combinations on IOP in the normal NZW rabbit.

Upon gross observation and subjective grading, phenylephrine greatly attenuated the hyperemia produced by compounds I. Phenylephrine at a low concentration (0.12%) enhances both the IOP lowering effect and duration of activity of compounds I. This effect is enhanced by increasing the concentration of phenylephrine to 1%.

TABLE 1

| Drug conc. | Phenylephrine concentration | N (no. of subjects) | Maximal % reduction outflow pressure (ROP) (mean ± S.E.M.) | Time of maximal % ROP (hour) | Times post-administration of significant ROP (hour) |
|---|---|---|---|---|---|
| A, 0.1% | 0% | 49 | 40.2 ± 3.3[a] | 1.5 | 0.5–5 |
| B, 1% | 0% | 42 | 34.2 ± 3.4[a] | 1 | 0.5–3 |
| none | 0.12% | 15 | 11.2 ± 1.5 | 3 | NSR[b] |
| A, 0.1% | 0.12% | 15 | 49.7 ± 4.5[a] | 1 | 0.5–7 |
| A, 0.1% | 1% | 5 | 73.8 ± 4.1[a] | 0.5 | 0.5–7 |
| B, 1% | 0.12% | 5 | 30.6 ± 10.4[a] | 0.5 | 0–1 |
| C, 0.1% | 0% | 5 | 66.2 ± 8.6[a] | 1 | 1–3 |
| C, 0.25% | 0% | 10 | 53.1 ± 5.8[a] | 1 | 1–4 |
| C, 0.25% | 0.12% | 5 | 65.0 ± 13.9[a] | 1 | 0.5–5 |
| D, 0.1% | 0.0% | 15 | 35.6 ± 10.3[a] | 0.5 | 0.5–2 |
| D, 0.1% | 0.12% | 5 | 31.4 ± 11.0[a] | 6 | 4–8 |
| E, 0.1 | 0% | 15 | 52.5 ± 9.5[a] | 1 | 0.5–4 |
| E, 0.1 | 0.12% | 10 | 45.6 ± 12.0[a] | 3 | 2–6 |
| F, 0.25 | 0% | 5 | 50.4 ± 4.0[a] | 3 | 0.5–6 |
| F, 0.25 | 0.12% | 5 | 39.8 ± 6.0[a] | 5 | 3–7 |
| G, 0.25 | 0% | 5 | 33.6 ± 10.6[a] | 4 | 4–5 |
| G, 0.25 | 0.12% | 5 | 50.2 ± 7.1[a] | 6 | 3–8 |

[Notes]
The compounds designated A through G in the above table are as follows:
A: 7β-desacetyl-7β-(2,3-dihydroxypropionyl)forskolin
B: forskolin, namely, 7β-acetoxy-8,13-epoxy-1α,6β,9α-trihydroxylabd-14-en-11-one.
C: 7β-desacetyl-7β-(methylaminocarbonyl)forskolin
D: 7β-desacetyl-6β-(tetrahydrofurano-2-yl)forskolin
E: 7β-desacetyl-6β-(2,3-dihydroxypropionyl)forskolin
F: 7β-desacetyl 7β-[N—(2,3-dihydroxypropyl)aminocarbonyl]-forskolin
G: 7β-desacetyl-7β-trimethylacetylhydroxylaminocarbonylforskolin
[a]Significantly different from pretreatment reading as determined by the paired Students t-test; P <0.05.
[b]No significant reduction.

A similar test was conducted using normal Dutch Belt rabbits. The results are summarized in Table 2.

TABLE 2

| Drug conc. | Phenylephrine concentration | N (no. of subjects) | Maximal % reduction outflow pressure (ROP) (mean ± S.E.M.) | Time of maximal % ROP (hour) | Times post-administration of significant ROP (hour) |
|---|---|---|---|---|---|
| A, 0.1% | 0% | 5 | 28.2 ± 7.5[a] | 1 | 0.5–3 |
| A, 0.5% | 0% | 14 | 17.5 ± 5.1[a] | 1 | 0–1 |
| A, 1.0% | 0% | 5 | 40.0 ± 7.4[a] | 3 | 1.5–8 |
| A, 0.1% | 0.12% | 5 | 26.8 ± 7.8[a] | 9 | 7–9 |
| A, 0.25% | 0.12% | 10 | 20.1 ± 4.8[a] | 8 | 4–8 |
| A, 0.5% | 0.12% | 5 | 61.0 ± 13.2[a] | 6 | 2–24 |
| A, 1.0% | 0.12% | 10 | 47.9 ± 10.3[a] | 10 | 2–24 |
| A, 2.0% | 0.12% | 5 | 54.6 ± 8.8[a] | 6 | 3–8 |
| C, 0.1% | 0% | 10 | 17.4 ± 4.5[a] | 1.5 | 1–2 |
| C, 0.25% | 0% | 5 | 21.4 ± 3.2[a] | 3 | 2–4 |
| C, 0.1% | 0.12% | 5 | 38.6 ± 8.0[a] | 1.5 | 1–6 |
| C, 0.25% | 0.12% | 5 | 46.6 ± 13.4[a] | 1.5 | 1–6 |
| C, 0.5% | 0.12% | 5 | 34.0 ± 5.1[a] | 4 | 1–6 |
| H, 0.25 | 0% | 5 | 25.4 ± 7.0[a] | 5 | 5–6 |

TABLE 2-continued

| Drug conc. | Phenylephrine concentration | N (no. of subjects) | Maximal % reduction outflow pressure (ROP) (mean ± S.E.M.) | Time of maximal % ROP (hour) | Times post-administration of significant ROP (hour) |
|---|---|---|---|---|---|
| H, 0.25% | 0.12% | 5 | 38.0 ± 4.0[a] | 4 | 3–7 |
| I, 0.25% | 0% | 5 | 17.8 ± 3.0[a] | 2 | 2–5 |
| I, 0.25% | 0.12% | 5 | 48.0 ± 11.0[a] | 7 | 3–7 |

[Notes]
The compounds designated H and I in the above table are as follows:
H: 7β-desacetyl-7β-(2-hydroxyethylaminocarbonyl)forskolin
I: 7β-desacetyl-7β-hydroxyaminocarbonylforskolin
[a]Significantly different from pretreatment reading as determined by the paired Students t-test, P <0.05.

We claim:

1. A synergistic intraocular pressure lowering composition for topical application comprising a suitable vehicle and effective hyperemia suppressing and intraocular pressure lowering amounts of an ocular decongestant and a compound having the formula

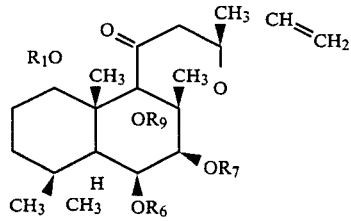

wherein
(a) $R_1$ is —H,

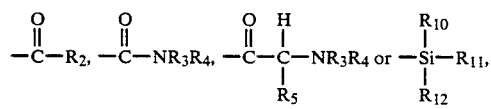

where
$R_2$ is hydrogen, loweralkyl,

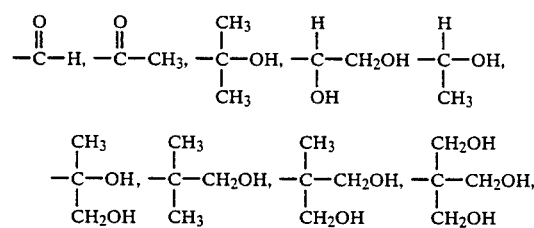

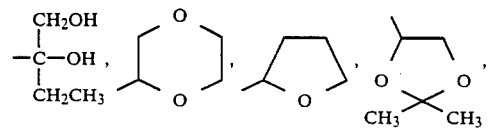

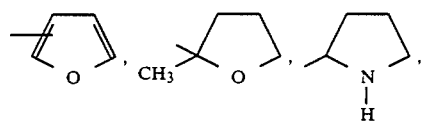

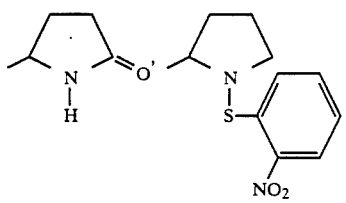

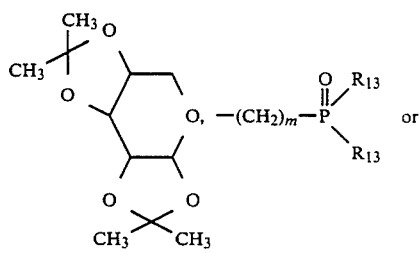

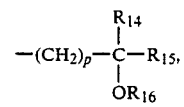

where
m is 1, 2 or 3, $R_{13}$ is loweralkyl, p is 0, 1, 2 or 3, $R_{14}$, $R_{15}$ and $R_{16}$ are each independently hydrogen or loweralkyl;
$R_3$ is hydrogen, loweralkyl, —(CH$_2$)$_q$OR$_{17}$ or —CH$_2$CHOHCH$_2$OH, where q is 0, 2 or 3 and $R_{17}$ is hydrogen or loweralkyl; $R_4$ is hydrogen, loweralkyl or —(CH$_2$)$_r$OH where r is 2 or 3, or alternatively —NR$_3$R$_4$ as a whole is

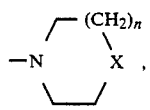

where n is 0, 1 or 2 and —X— is

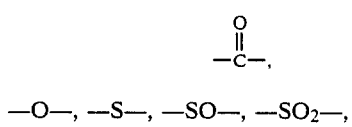

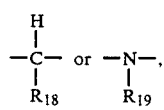

$R_{18}$ being hydrogen, loweralkyl, loweralkoxy or loweralkylcarbonyloxy, and $R_{19}$ being loweralkyl;

$R_5$ is hydrogen, loweralkyl, benzyl or hydroxymethyl; and $R_{10}$, $R_{11}$ and $R_{12}$ are each independently loweralkyl;

(b) $R_9$ is hydrogen, or alternatively to the above, $R_1$ and $R_9$ taken together form $$-\overset{O}{\underset{\|}{C}}-, \quad -\overset{O}{\underset{\|}{S}}- \quad \text{or} \quad -\overset{H}{\underset{NR_{20}R_{21}}{\overset{|}{C}}}-,$$

where $R_{20}$ and $R_{21}$ are each independently loweralkyl, or alternatively $-NR_{20}R_{21}$ as a whole is $$-N\overset{(CH_2)_{n'}}{\underset{\diagdown}{\diagup}}X',$$

where n′ has the same definition as n but is independent thereof and X′ has the same definition as X but is independent thereof; and (c) $R_6$ and $R_7$ are each independently —H, $$-\overset{O}{\underset{\|}{C}}-R'_2, \quad -\overset{O}{\underset{\|}{C}}-NR'_3R'_4 \quad \text{or} \quad -\overset{O}{\underset{\|}{C}}-\overset{H}{\underset{R'_5}{\overset{|}{C}}}-NR'_3R'_4,$$

or taken together form $$-\overset{O}{\underset{\|}{C}}- \quad \text{or} \quad -\overset{O}{\underset{\|}{S}}-,$$

where $R_2'$, $R_3'$, $R_4'$ and $R_5'$ have the same definitions as $R_2$, $R_3$, $R_4$ and $R_5$, respectively, but are independent thereof.

2. The synergistic intraocular pressure lowering composition as defined in claim 1, wherein the ocular decongestant is phenylephrine.

3. The synergistic intraocular pressure lowering composition as defined in claim 1, wherein the ocular decongestant is phenylephrine and the compound is 7β-desacetyl-7α-(2,3-dihydroxypropionyl)forskolin.

4. The synergistic intraocular pressure lowering composition as defined in claim 1, wherein the ocular decongestant is phenylephrine and the compound is 7β-desacetyl-7β-(methylaminocarbonyl)forskolin.

5. The synergistic intraocular pressure lowering composition as defined in claim 1, which comprises an effective amount of 7β-desacetyl-7β-(2,3-dihydroxypropionyl)forskolin.

6. The synergistic intraocular pressure lowering composition as defined in claim 1, which comprises an effective amount of 7β-acetoxy-8,13-epoxy-1α,6β,9α-trihydroxylabd-14-en-11-one.

7. The synergistic intraocular pressure lowering composition as defined in claim 1, which comprises an effective amount of 7β-desacetyl-7β-(methylaminocarbonyl)forskolin.

8. The synergistic intraocular pressure lowering composition as defined in claim 1, which comprises an effective amount of 7β-desacetyl-6β-(tetrahydrofurano-2-yl)forskolin.

9. The synergistic intraocular pressure lowering composition as defined in claim 1, which comprises an effective amount of 7β-desacetyl-6β-(2,3-dihydroxypropionyl)forskolin.

10. The synergistic intraocular pressure lowering composition as defined in claim 1, which comprises an effective amount of 7β-desacetyl-7β-(2-hydroxyethylaminocarbonyl)forskolin.

11. The synergistic intraocular pressure lowering composition as defined in claim 1, which comprises an effective amount of 7β-desacetyl-7β-hydroxyaminocarbonylforskolin.

12. A method of lowering intraocular pressure without causing substantial redness in the eye of a mammal including human, which comprises lowering the intraocular pressure of said eye by topical administration of an effective amount of the synergistic intraocular pressure lowering composition as defined in claim 1.

13. A method of lowering intraocular pressure without causing substantial redness in the eye of a mammal including human, which comprises lowering the intraocular pressure by topical administration of an effective amount of the synergistic intraocular pressure lowering composition as defined in claim 2.

14. A method of lowering intraocular pressure without causing substantial redness in the eye of a mammal including human, which comprises lowering the intraocular pressure by topical administration of an effective amount of the synergistic intraocular pressure lowering composition as defined in claim 3.

15. A method of lowering intraocular pressure without causing substantial redness in the eye of a mammal including human, which comprises lowering the intraocular pressure of said eye by topical administration of an effective amount of the synergistic intraocular pressure lowering composition as defined in claim 4.

16. The method as defined in claim 12, wherein the synergistic intraocular pressure lowering composition comprises 7β-desacetyl-7β-(2,3-dihydroxypropionyl)-forskolin.

17. The method as defined in claim 12, wherein the synergistic intraocular pressure lowering composition comprises 7β-acetoxy-8,13-epoxy-1α,6β,9α-trihydroxylabd-14-en-11-one.

18. The method as defined in claim 12, wherein the synergistic intraocular pressure lowering composition comprises 7β-desacetyl-7β-(methylaminocarbonyl)forskolin.

19. The method as defined in claim 12, wherein the synergistic intraocular pressure lowering composition comprises 7β-desacetyl-6β-(tetrahydrofurano-2-yl)forskolin.

20. The method as defined in claim 12, wherein the synergistic intraocular pressure lowering composition comprises 7β-desacetyl-6β-(2,3-dihydroxypropionyl)-forskolin.

21. The method as defined in claim 12, wherein the synergistic intraocular pressure lowering composition comprises 7β-desacetyl-7β-trimethylacetylhydroxylaminocarbonylforskolin.

22. The method as defined in claim 12, wherein the synergistic intraocular pressure lowering composition comprises 7β-desacetyl-7β-(2-hydroxyethylaminocarbonyl)forskolin.

23. The method as defined in claim 12, wherein the synergistic intraocular pressure lowering composition comprises 7β-desacetyl-7β-hydroxyaminocarbonylforskolin.

24. The synergistic intraocular pressure lowering composition as defined in claim 1, which comprises an effective amount of 7β-desacetyl-7β-[N-(2,3-dihydroxypropyl)aminocarbonyl]forskolin.

25. The synergistic intraocular pressure lowering composition as defined in claim 1, which comprises an effective amount of 7β-desacetyl-7β-trimethylacetylhydroxylaminocarbonylforskolin.

26. The synergistic intraocular pressure lowering composition as defined in claim 1, which comprises an effective amount of 7β-desacetyl-7β-[(4-hydroxypiperidinyl)carbonyl]forskolin.

27. The method as defined in claim 12, wherein the synergistic intraocular pressure lowering composition comprises 7β-desacetyl-7β-[N-(2,3-dihydroxypropyl)aminocarbonyl]forskolin.

28. The method as defined in claim 12, wherein the synergistic intraocular pressure lowering composition comprises 7β-desacetyl-7β-[(4-hydroxypiperidinyl)carbonyl]forskolin.

* * * * *